United States Patent [19]

Yang et al.

[11] Patent Number: 4,695,463

[45] Date of Patent: Sep. 22, 1987

[54] DELIVERY SYSTEM FOR ACTIVE INGREDIENTS AND PREPARATION THEREOF

[75] Inventors: Robert K. Yang, Randolph; Shri C. Sharma, Mendham, both of N.J.

[73] Assignee: Warner-Lambert Company, Morris Plains, N.J.

[21] Appl. No.: 738,148

[22] Filed: May 24, 1985

[51] Int. Cl.⁴ .................. A61K 47/00; A23G 3/30; A01N 43/00
[52] U.S. Cl. .................................... 424/440; 426/3; 424/488; 424/48; 427/3; 523/120; 514/779; 514/783; 514/965
[58] Field of Search ............. 426/3; 523/120; 514/965, 779, 783; 424/48, 22, 35, 440, 488; 427/3

[56] References Cited

U.S. PATENT DOCUMENTS

| | | | |
|---|---|---|---|
| 3,201,353 | 8/1965 | Corben | 264/41 |
| 3,632,739 | 1/1972 | Kornblum | 424/22 |
| 3,764,707 | 10/1973 | Habersberger | 514/779 |
| 3,857,964 | 12/1974 | Yolles et al. | 426/3 |
| 3,930,026 | 12/1975 | Clark | 426/3 |
| 3,962,463 | 6/1976 | Witzel | 426/3 |
| 3,985,913 | 10/1976 | Johnson et al. | 426/650 |
| 4,065,579 | 12/1977 | Mackay et al. | 426/3 |
| 4,238,475 | 12/1980 | Witzel et al. | 424/48 |
| 4,259,355 | 3/1981 | Marmo et al. | 426/5 |
| 4,328,475 | 5/1982 | Clark | 334/7 |
| 4,386,106 | 5/1983 | Merritt et al. | 426/5 |
| 4,389,419 | 6/1983 | Lim et al. | 426/72 |
| 4,401,456 | 8/1983 | Connick | 514/779 |
| 4,448,789 | 5/1984 | Yang | 426/5 |
| 4,505,935 | 3/1985 | Larsson | 514/779 |
| 4,568,560 | 2/1986 | Schobel | 426/5 |
| 4,569,852 | 2/1986 | Yang | 426/534 |

FOREIGN PATENT DOCUMENTS 40048 11/1981 European Pat. Off. .

Primary Examiner—Ronald W. Griffin
Attorney, Agent, or Firm—Daniel A. Scola, Jr.; Gary M. Nath

[57] ABSTRACT

A delivery system useful in chewing gum, confectionary and pharmaceutical products comprising:
(a) an insolubolized active ingredient; and
(b) a cross-linked hydrocolloid multivalent cation alginate or carageenenate matrix entrapping said insolubolized active ingredient.

A process of preparation is also disclosed.

26 Claims, 1 Drawing Figure

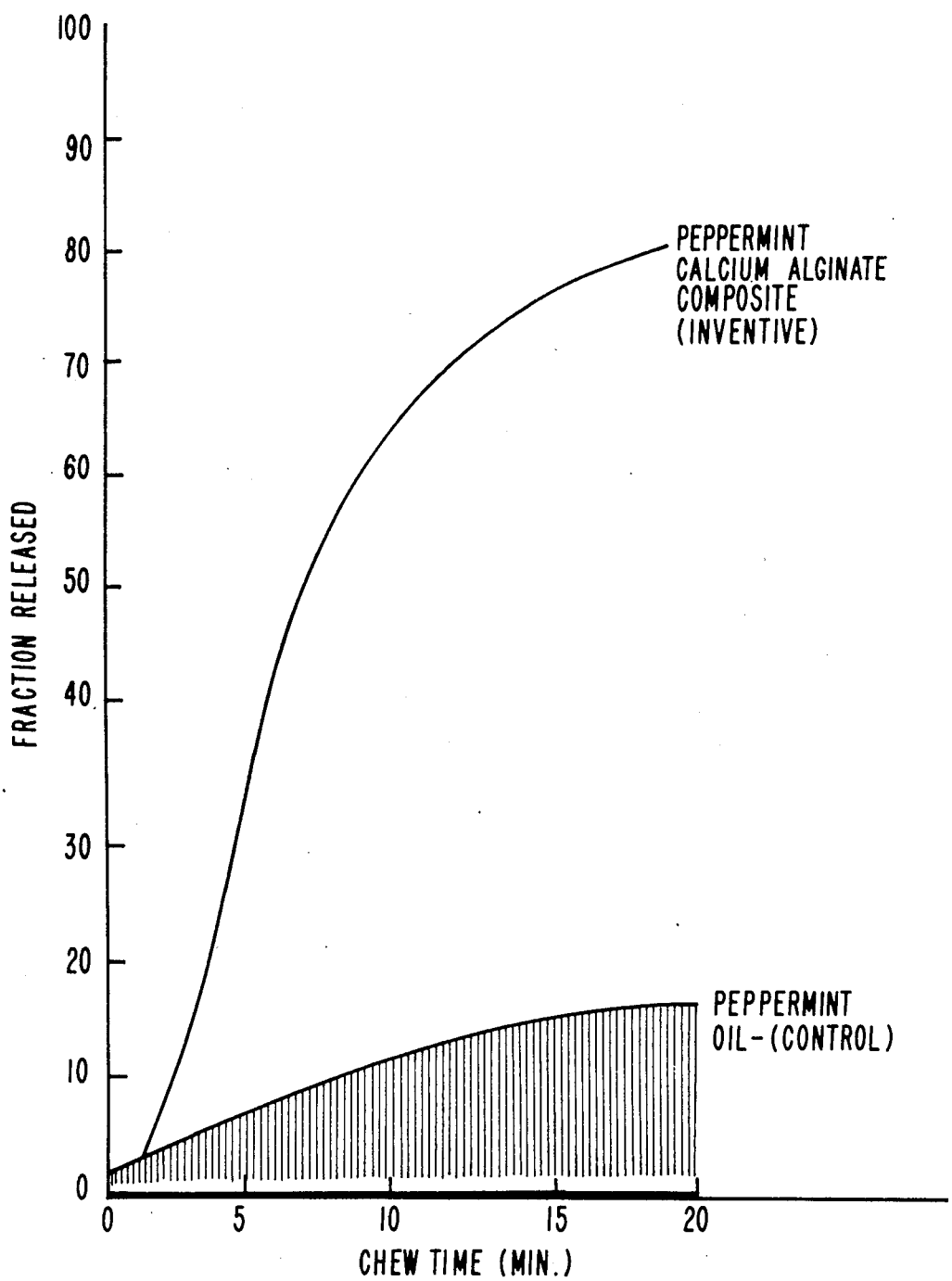

DELIVERY SYSTEM FOR ACTIVE INGREDIENTS AND PREPARATION THEREOF

This invention relates to delivery systems for active ingredients and methods of their preparation. Specifically, the delivery system provides a means for entrapping active ingredients in a hydrocolloid matrix such that when the delivery system is incorporated in a variety of vehicles such as chewing gum compositions, the release of the active ingredient is prolonged and controlled.

It is well known that with most flavored chewing gum compositions, the perception of flavor drops sharply after a short initial period of chewing. It is also known that large amounts of flavor incorporated into chewing gums are retained within the bolus and are never released during mastication. The bolus, primarily comprised of elastomers, resins and waxes, can entrap as much as 90% of the flavor. The remainder of the flavor which is available for release is generally physically associated with the water soluble chewing gum components, e.g., carbohydrates (particularly sweeteners), softeners and the like. To compensate for the unavailable flavor lost to the bolus and obtain a desired level of flavor intensity it is sometimes necessary to add higher amounts than normal of sweetener to the chewing gum. This has not resulted in acceptable flavoring, particularly in mint gums, because of harsh notes and bitterness which became apparent at higher levels. Additionally, excess amounts of flavoring ingredients tend to soften and plasticize the gum base, thereby affecting the chew characteristics.

Various coating and encapsulating materials and techniques have been used to trap active ingredients such as flavors and control their release. More specifically, U.S. Pat. No. 3,962,463 discloses hydrocolloid materials, such as solutions of gum and alginates which are used to microencapsulate flavor particles. The slurry of flavor particles are then used as a surface coating for the gum. U.S. Pat. No. 3,930,026 discloses a chewing gum having flavor and surfactant sorbed on a hydrocolloid substrate, which is then incorporated into a gum base for enhanced flavor. U.S. Pat. Nos. 3,985,913, 3,857,964 and 4,238,475 disclose the use of alginates as a spray coating for flavor particles using standard spray drying techniques. U.S. Pat. No. 4,065,579 discloses sodium alginates as a useful coating for chalk-containing gum base. Additionally, European Patent Application 81392918.3 discloses the use of calcium alginate fibers for encapsulation flavors in chewing gum and candy. The algin and calcium solutions are disclosed as producing instantaneous cross-linking at room temperature providing the pH is kept at 4.2 prior to addition of the calcium ion. The tightly crosslinked alginate fibers allegedly squeeze water and other small molecules out during precipition. Larger molecular weight ingredients such as water soluble gums, carbohydrates, protein or flavor oils remain trapped in the fiber.

Heretofore, the art has not disclosed a method which effectively prevents flavor and other active ingredients from becoming trapped in the gum base. The inventive compositions and process provide a unique means of preventing the loss of flavor or other active ingredient to the gum base. Eighty percent or more of the flavor content is now available for release due to the entrapment of flavor in a novel delivery system. The flavor intensity of the vehicle containing the delivery system, e.g., chewing gum, is greatly enhanced due to the significantly higher amounts of flavor released. About six to eight times as much flavor than the prior art chewing gum compositions is now released during chew, thereby allowing for smaller total quantities of flavor to be used in the composition. Additionally, the prolongation of flavor and enhancement of sweetness is also significantly more pronounced than the prior art compositions. The problems of the prior art cited above are thus avoided, creating a chewing gum composition with long-lasting, uniform flavor levels.

More particularly, the instant invention concerns a delivery system comprising:

(a) an insolubolized active ingredient; and
(b) a cross-linked alginate or carageenenate matrix entrapping said insolubolized active ingredient.

The term "insolubolized" is meant to include supersaturated solutions. Thus, the active may include water-soluble as well as water-insoluble or hydrophobic and hydrophilic materials. For example, a supersaturated solution of water-soluble active will have particles of the active ingredient dispersed in the saturated solution. Thus, it is essential to the invention that the active ingredient and the monovalent aqueous hydrocolloid solution be capable of cooperating to form a dispersion. For purposes of this invention, "dispersion" can mean a liquid, solid or gaseous dispersion.

The invention uses the unique properties of the algins and carageenens to trap the active ingredient. Certain hydrocolloids, such as monovalent alginates and carageenen salts are capable of undergoing ion substitutions with multivalent salts. Thus, multivalent cations such as calcium or magnesium can be substituted for sodium or potassium ions by combining the multivalent cations with the monovalent algins and carageenen. While it is preferred that both mono- and multivalent cations type of ions be in solution prior to combining them, it is also useful to add the multivalent cation directly to an aqueous solution of the monovalent hydrocolloid. For example, a multivalent cation salt or hydroxy compound, such as calcium chloride or calcium carbonate, can be added in solid form to the monovalent solution. During the cation substitution, the physical phase as well as the properties of the system changes. As more monovalent cations are replaced by multivalent cations, the solution changes to a gel-like phase. Once the ion substitute is substantially complete, the gel becomes a water insoluble and irreversible precipitate. While cross-linking is preferably due to the exchange of ions, it is also accomplished by the manipulation of pH. Thus, the addition of acid will also initiate cross-linking.

More particularly, the insolubolized active ingredient is suspended in an aqueous solution of a monovalent cation salt of an algin and/or carageenen hydrocolloids. To this solution is added a precipitate initiating material, e.g., a multivalent cation, multivalent cation-containing compound, or an acid.

Examples of useful multivalent cations include aluminum, calcium, iron, magnesium, manganese, copper, zinc and the like and mixtures thereof. The cations are ordinarily part of a compound and preferably a salt or hydroxy compound. The addition of the multivalent cation to the dispersion results in the exchange of multivalent for monovalent cation within the hydrocolloid complex and a crosslinked matrix manifested by an insoluble precipitate is formed. It is during the formation of this precipitate that the active ingredient becomes entrapped within the matrix. Examples of useful precipitate initiating acids include inorganic as well as organic acids. Inorganic acids are preferred and may be selected from numerous food grade compounds. Hydrochloric, nitric, sulfuric and phosphoric are preferred, although numerous others are contemplated.

The matrix of the composite is not soluble in hydrophobic vehicles such as gum base and hence prevents migration and subsequent entrapment of the flavor in the gum bolus. Rather, the composite matrix is substantially impermeable to water insoluble materials. Thus, the matrix structure prevents migration of the flavor onto the gum base as well as preventing gum base materials from penetrating into the flavor oil.

Those hydrocolloid materials useful in forming the composite matrix must be capable of swelling when hydrated and change from a solution to a gel to a precipitate during the chemical exchange of the bivalent ion for monovalent ion. Among those useful materials are monovalent salts of algins and carageenens. Algins are long linear copolymers of D-mannuronic acid or L-guluronic acid, having molecular weights ranging from about 4,000 to about 180,000. The carageenens are derived from seaweed. The sodium, potassium and lithium salts of the algins and the carageenens are water soluble and are therefore useful. Other salts are contemplated. These monovalent metal cations are readily displaced by multivalent cations such as aluminum, iron, calcium, magnesium, manganese, copper and zinc and the like, which in turn react with carboxylic acid groups of the hydrocolloid to form a cross-linked matrix. While the aforementioned multivalent ions are all contemplated for use in this invention, the preferred ions are bivalent, and the preferred bivalent cation is calcium. The multivalent cations are generally added to the monovalent hydrocolloid solution in the salt form. For example, calcium chloride is the preferred multivalent cation material. However, other compounds containing multivalent cations are useful; For example, hydroxy compound such as calcium carbonate, magnesium carbonate and the like. The initial stage of cross-linking manifests itself in the formation of a gel or gel-like material. As additional monovalent ions are replaced, crosslinking continues until an insoluble precipitate results.

As previously mentioned, while the multivalent cation compound may be added in particulate form to the monovalent cation/insolubolized active dispersion, it is preferably added as an aqueous solution. In preparing the solution of the water soluble hydrocolloid monovalent salt, the hydrocolloid comprises about 1% to about 5% and preferably about 2% to about 4% by weight of the solution. The weight ratio of the hydrocolloid matrix to insolubolized active is about 5:1 to about 1:2, and preferably about 2:1 to about 1:1. If the multivalent cation is to be added in aqueous solution, the concentration ranges from about 1% to about 10% by weight and preferably about 2% to about 8%.

One embodiment of the process of preparing the delivery system comprises:
(a) forming an aqueous suspension of a monovalent cation algin or carageenen salt and an insolubolized active ingredient;
(b) combining the aqueous suspension of the insolubolized active ingredient with a precipitate initiating material; and
(c) recovering a precipitated product and drying to form the delivery system.

As previously stated, the preferred monovalent hydrocolloid salts are the water-soluble sodium, potassium and lithium salts of algins and carageenens. Sodium alginate is the preferred monovalent salt. While active ingredients may be added to the monovalent salt solution at room temperature, it is preferred that the solution be cooled before addition of the active ingredient, in order to avoid any volatization. This is particularly true if the active ingredient is a flavor oil. Temperatures ranging from about 0° C. to about 20° C., and preferably about 2° C. to about 8° C. may be used, providing however, that the solution does not crystallize or freeze. In one embodiment of the process, high shear mixing is used to uniformly disperse the active ingredient within the solution. Caution must be used to chose the correct speed and mixing time in order to achieve uniformity. Mixing for too long a time may reduce the viscosity by shearing the monovalent hydrocolloid salt to a point where its effectiveness as a means of entrapping the active ingredient during ion exchange is substantially reduced. On the other hand, high shear mixing for too short a time results in large droplets or particles of active which are difficult to entrap in the interstices of the matrix. The particle or droplet size of the active should be a maximum of about 10 microns, although the range below that may vary. For best results, the average particle size of the dispersed particles or droplets should be about 1 to about 5 microns.

Thus, in the above embodiment it is apparent that a delicate balance of mixing time and speed must be maintained for proper uniformity of dispersion. Additionally, if too high a shear speed is used for too long, localized heat buildup in the dispersion may cause volatilization of the active ingredient. To protect against localized heat buildup, the temperature of the dispersion should be maintained at about 0° to about 20° C. Generally, about four to ten minutes is a proper shearing time and the mixing speed may vary from about 30 to about 7,500 RPM on a standard Eppenbach homo-head mixer. Other suitable mixing equipment such as colloid millers, etc., can also be used.

The multivalent cation compound must be capable of ionizing in water. Nonlimiting examples of useful compounds are the chloride, sulfate, acetate and carboxylate salts of calcium, magnesium, copper, zinc, manganese, aluminum, iron and the like. Other useful multivalent compounds such as hydroxy compounds, carbonates and the like, are contemplated, as well as mixtures thereof.

In an alternative embodiment of the process, the multivalent cation solution can be added to the monovalent cation/insolubolized active dispersion by spraying the one into the other. Preferably the multivalent cation, for example, calcium chloride solution, is sprayed from a nozzle in the form of a fine spray into the dispersion. The spray naturally contains the active ingredient within. Once the fine spray contacts the dispersion, precipitate rapidly forms entrapping the active ingredient within the thus formed matrix. The advantage to this embodiment is that mixing of the final mixture is not necessary, since the spray droplet size can be controlled within the preferred range to ensure sufficient intimate contact and cation exchange.

The multivalent cation may be added to the dispersion in stochiometric amounts relative to the concentration of monovalent ion present, but preferably excess multivalent cations are added to insure substantially complete replacement of the monovalent cation with the multivalent cation in the hydrocolloid structure. The addition of the multivalent cation should be carried out at a temperature which are lower than the point at which the active ingredient will begin to volatize. Preferably, the addition is carried out at temperatures of about 1° to about 20° C. and most preferably about 1° to about 5° C. The addition should be carried out in a relatively rapid continuous manner using the shortest shearing time possible to get as much flavor exposed to and entrapped by the matrix which forms in situ. Unless the addition of the multivalent cation is by spray or fine droplet, mixing is necessary for best results, in order to homogenize the dispersion and allow the multivalent cations to come in contact with and replace the monovalent cations.

The formation of the hydrocolloid matrix is manifested by the irreversible, insoluble precipitate which is formed. The precipitate is then filtered off, washed and dried. Drying of the matrix may be carried out by conventional methods such as air drying at room temperature or freeze drying. Drying at temperatures above the volatilization point of the active ingredient is not recommended. Generally, drying should be carried out at temperatures of about 25° C. or less. A preferred drying method is to use a combination of freeze drying followed by room temperature air drying. Once dried, the matrix is brittle and easily ground into particles of various sizes. These particles comprise what is referred to as the delivery system. Particle size may vary with a particular application and can be easily determined by routine experimentation. As previously mentioned, if the alternative spraying process is used, grinding may be unnecessary since the particles comprising the delivery system may already be within a suitable size range. In chewing gum compositions, for example, the delivery system may have an average size about 30 to about 150 U.S. standard mesh (about 590 to about 105 microns) and preferably about 40 to about 60 mesh (about 420 to about 250 microns).

As previously stated, suitable active ingredients may be selected from a wide range of materials. The only requirement is that they be capable of being in the insolubolized state when placed in the monovalent cation hydrocolloid solution. In other words, they must be ultimately capable of being dispersed within the solution. Thus, substantially insoluble or hydrophobic materials as well as substantially soluble and hydrophillic materials are operable. In the case of hydrophillic materials, a supersaturated solution is contemplated whereby sufficient excess active ingredient is present in the monovalent cation hydrocolloid salt solution such that a dispersion results. Acid saccharin is an example of a poorly water-soluble material which works well in the instant invention. The aluminum salt of saccharin is another such material. By maintaining a low temperature of the solution, a supersaturated solution using these materials is created. The active which does not become solubolized remains dispersed.

Examples of flavoring agents useful as the active ingredient include the synthetic and natural flavor oils, fruit essences and various extracts. For example: spearmint oil, peppermint oil, cinnamon oil, oil of wintergreen (methylsalicylate); citrus oils such as lemon, orange, grape, lime, grapefruit and the like; fruit essences such as apple, strawberry, cherry, pineapple, and so forth; and extracts such as kola extract. Mixtures of these are also contemplated.

Examples of useful drugs which may be useful as the active ingredient include: mineral supplements, analgesics, antipyretics, antiarrhythmics, ion exchange resins, appetite supressants, vitamins, anti-inflammatory substances, coronary dilators, cerebral dilators, peripheral vasodilators, anti-infectives, psychotropics, antimanics, stimulants, antihistamines, laxatives, decongestants, gastro-intestinal sedatives, antidiarrheal preparations, antianginal drugs, vasodilators, antiarrythmics, anti-hypertensive drugs, vasoconstrictors and migrane treatments, antibiotics, tranquilizers, antipsychotics, antitumor drugs, anticoagulants and antithrombotic drugs, hypnotics, sedatives, antiemetics, anti-nauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, anti-uricemic drugs and mixtures thereof.

Useful coloring agents and fragrances may be selected from any of these suitable for use in food, drug and cosmetic applications, providing they are capable of being dispersed in the manner previously recited.

Sweetening agents are also useful as active ingredients. Due to the high water solubility of most of these materials, a supersaturated solution will ordinarily be necessary in order to obtain the requisite dispersion. As previously mentioned, however, poorly soluble sweeteners, such as the acid saccharin, work particularly well. Any of the sweeteners mentioned in connection with the vehicles later to be described may be used.

The delivery system may be used in a variety of products or vehicles including chewing gum and confectionery products, pharmaceutical preparations, food products, tobacco and proprietary products such as toothpaste, denture adhesives and the like.

If the delivery system is used in chewing gum formulations, the amount of gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 15% to about 25% by weight. The gum base may be any water-insoluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong, gutta percha and crown gum. Synthetic elastomers such as butadienestyrene copolymers, isobutylene-isoprene copolymers, polyethylene, polyisobutyliene and polyvinylacetate and mixtures thereof, are particularly useful.

The gum base composition may contain elastomer solvents or plasticizers to aid in softening the rubber component. Such elastomer solvents may comprise methyl, glycerol or pentaerythritol esters of rosins and gums or modified rosins and gums, such as hydrogenated, dimerized or polymerized rosins and gums or mixtures thereof. Examples of elastomer solvents suitable for use herein include the pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of -pinene or -pinene; terpene resins including polyterpene and mixtures thereof. The solvent may be employed in an amount ranging from about 10% to about 75% and preferable about 45% to about 70% by weight to the gum base.

A variety of traditional ingredients such as plasticizers or softeners such as lanolin, stearic acid, sodium stearate, potassium stearate, glyceryl triacetate, glycerine and the like for example, natural waxes, petroleum waxes, such as polyurethere waxes, paraffin waxes and microcrystalline waxes may also be incorporated into the gum base to obtain a variety of desirble textures and consistency properties. These individual additional materials are generally employed in amounts of up to about 30% by weight and preferably in amounts of from about 3% to about 20% by weight of the final gum base composition.

The gum compositions generally contain a major portion of a sweetening agent. These sweetening agents are independent from the excipients and sweetening agents used in the delivery system described above. Sweetening agents may be selected from a wide range of materials such as water-soluble sweetening agents, water soluble artificial sweeteners, and dipeptide based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, invert sugar, maltose, partially hydrolyzed starch, or corn syrup solids and sugar alcohols such as sorbitol, xylitol, mannitol, dihydrochalcone, glycyrrhizin, *stevia rebaudiana* (stevioside) and mixtures thereof.

B. Water-soluble artificial sweeteners such as the soluble saccharin salts, i.e. sodium or calcium saccharin salts, cyclamate salts and the like; the free acid form of saccharin; the synthetic sweetener 3,6-dehydro-6-methyl-1-1,2,3-oxathiazin-4-one-2,2-dioxide, particularly the potassium acesulfame-K), sodium and calcium salts thereof as described in German Pat. No. 2,001,017.7.

C. Dipeptide based sweeteners include L-aspartyl-L-phenylalanine methyl ester and materials described in U.S. Pat. No. 3,492,131 and the like.

In general, the amount of sweetener will vary with the desired amount of sweetener selected for a particular chewing gum composition. This amount will normally be about 0.01% to about 90% by weight when using an easily extractable sweetener. The water-soluble sweeteners are preferably used in amounts of about 25% to about 75% by weight, and most preferably about 50% to about 65% by weight of the final chewing gum composition.

In contrast, the artificial sweeteners described in categories B and C are used in amount of about 0.01 to about 5.0% and most preferably about 0.05% to about 0.50% by weight of the final chewing gum composition. These amounts are necessary to achieve a desired level of sweetness independent from the flavor level achieved from the flavor oil.

Flavoring agents in addition to those incorporated in the delivery system may be added to the chewing gum compositions of the instant invention. These flavoring agents may be chosen from synthetic flavoring liquids and/or liquids derived from plants, leaves, flowers, fruits and so forth, and combinations thereof. Representative flavoring liquids include: spearmint oil, cinnamon oil, oil of wintergreen (methylsalicylate) and peppermint oils. Also useful are artificial, natural or synthetic fruit flavors such as citrus oil including lemon, orange, grape, lime and grapefruit and fruit essences including apple, strawberry, cherry, pineapple and so forth. Powdered flavoring, beaded flavoring, spray dried flavoring and encapsulated flavoring may also be added.

The amount of flavoring agent employed is normally a matter of preference subject to such factors as flavor type, base type and strength desired. In general, amounts of about 0.05% to about 3.0% by weight of the final chewing gum composition are usable with amounts of about 0.3% to about 1.5% being preferred and about 0.7% to about 1.2% being most preferred.

The colorants useful in the present invention, include the pigments such as titanium dioxide, that may be incorporated in amounts of up to about 1% by weight, and preferably up to about 0.6% by weight. Also, the colorants may include other dies suitable for food, drug and cosmetic applications, and known as F.D. & C. dyes and the like. The materials acceptable for the foregoing spectrum of use are preferably water-soluble. Illustrative examples include indigoid die, known as F.D. & C. Blue No. 2, which is the disodium salt of 5,5'-indigotindisulfonic acid. Similarly, the dye known as F.D. & C. Green No. 1, comprises a triphenylmethane dye and is the monosodium salt of 4-[4-Nethyl-p-sulfobenzylamino)diphenylmethylene]-[1-(N-ethyl-N-p-sulfoniumbenzyl)-2,5-cyclohexadienimine]. A full recitation of all F.D. & C. and D. & C. and their corresponding chemical structures may be found in the Kirk-Othmer Encyclopedia of Chemical Technology, in volume 5, at Pages 857–884, which text is accordingly incorporated herein by reference.

The delivery systems of this invention have excellent long term stability, i.e., more than 1 year at 37° C. The amount of active ingredient used in any given application will be purely a matter of preference of the user. The delivery systems of this invention are particularly advantageous because the release of active ingredient, for example, flavor, is gradual over an extended period of time. Since hydration is necessary in order to release the the active ingredient from the delivery system matrix, release of the active ingredient is delayed about 1 to about 6 minutes, generally about 2 to about 4 minutes once consumed or chewed. An initial burst of flavor can be obtained by adding auxilary active ingredients and excipients in conventional ways directly to the gum composition.

Once prepared the delivery system may be stored for future use or formulated with conventional additives, that is, pharmaceutically acceptable carriers and confectionery ingredients to prepare compositions which offer a variety of textures to suit particular applications. Such compositions may be in the form of a lozenge, tablet, toffee, nougat, chewy candy and so forth. The pharmaceutically acceptable carriers may be selected from a wide range of materials. Without being limited thereto, such materials include diluents, binders and adhesives, lubricants, disintegrants, colorants, flavorings, sweeteners and miscellaneous materials such as buffers and adsorbents in order to prepare a particular medicated composition. The preparation of confectionery and chewing gum products is historically well known.

Lozenges are flavored medicated dosage forms intended to be sucked and held in the mouth. They may be in the form of various shapes, the most common being flat, circular, octagonal and biconvex forms. The lozenge bases are generally in two forms, hard, boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having from 0.5 to 1.5% moisture. Such materials normally contain up to 92% corn syrup, up to 55% sugar and from 0.1% to 5.0% water. The syrup component generally is prepared from corn syrups high in fructose, but may include other materials. Further ingredients such as flavorings, sweeteners, acidulents, colorants and so forth may also be added. In contrast, compressed tablet lozenges contain particular materials and are formed into structures under pressure. They generally contain sugars in amounts up to 95% and typical tablet excipients such as binders and lubricants as well as flavors, colorants and so forth.

The lozenges may be made of soft confectionery materials such as those contained in nougat. These materials contain two primary components, namely a high boiling syrup such as corn syrup or the like, and a relatively light textured frappe, generally prepared from gelatin, egg albumen, milk proteins such as casein, and vegetable proteins such as soy protein, and the like. The frappe is generally relatively light, and may, for example, range in density from about 0.5 to about 0.7g/cc.

By comparison, the high boiling syrup, or "bob syrup", is relatively viscous and possesses a higher density, and frequently contains a substantial amount of sugar. Conventionally, the final nougat composition is prepared by the addition of the "bob syrup" to the frappe under agitation, to form the basic nougat mixture. Further ingredients such as flavorings, oils, additional sugar and the like may be added thereafter also under agitation. A general discussion of the composition and preparation of nougat confections may be found in B. W. Minifie, *CHOCOLATE, COCOA AND CONFECTIONERY: Science and Technology*, 2nd edition, AVI Publishing Co., Inc., Westport, Conn., (1980), at Pages 424–425.

Pharmaceutical tablets of this invention may also be chewable forms. This form is particularly advantageous because of convenience and patient acceptance and rapid onset of bioactivity. To achieve acceptable stability and quality as well as good taste and mouth feel several considerations are important, namely amount of active ingredient per tablet, flavor, compressibility and organoleptic properties of the drug.

The preparation of chewable medicated candy is prepared by procedures similar to those used to make soft confectionary. This procedure generally involves the formation of a boiled sugar-corn syrup blend to which is added a frappe mixture. The boiled sugar-corn syrup blend may be prepared from sugar and corn syrup blended in parts by weight ratio of 90 to 10:10 to 90. This blend is heated to temperatures above 250° F. to remove water and to form a molten mass. The frappe is generally prepared from gelatin, egg albumen, milk proteins such as casein, and vegetable proteins such as soy protein, and the like which are added to a gelatin solution and rapidly mixed at ambient temperature to form an aerated sponge like mass. The frappe is then added to the molten candy base and mixed until homogenous at temperatures between 150° F. and 250° F. The composite can then be added as the temperature of the mix is lowered below the melting point of the matrix whereupon additional ingredients are added such as flavors, and colorants. The formulation is further cooled and formed to pieces of desired dimensions.

A general discussion of the lozenge and chewable tablet forms of confectionery may be found in H. A. Lieberman and L. Lachman, *Pharmaceutical Dosage Forms: Tablets* Volume 1, Marcel Dekker, Inc., New York, N.Y. at pages 289 to 466.

The following examples serve to provide further appreciation of the invention but are not meant in any way to restrict the effective scope of the invention. All percentages throughout the specification are by weight % of the product unless otherwise indicated.

EXAMPLE I

This example demonstrates the method of preparation of the delivery system as well as use of flavor oil as the active ingredient to be entrapped.

Forty grams of a sodium alginate solution (having a viscosity of 115 centipose when measured in a 1% by weight aqueous solution at 75° C.) was dissolved in 1,600 ml of distilled water and chilled to 5° C. Forty grams of peppermint oil was then added to the solution with high shear mixing to form an oil in water dispersion. Using a Petroff-Hauses Chamber the oil droplets were determined to be within the 1 to 5 micron range.

With continued high shear mixing about 1,600 ml of a 2% by weight calcium chloride solution was added to the alginate solution. Mixing was continued for about 5 to about 10 minutes. As the displacement of the sodium ion by calcium ions occurred, the solution phase changed first to a gel-like consistency and then to a precipitate. The precipitate represented a crosslinked matrix resulting from ion exchange.

The cross-linked matrix was washed to remove excess calcium chloride solution and frozen at −15° C. overnight. After thawing, the calcium alginate matrix separated from the entrapped water. The matrix was filtered and air dried. The dried mass was comminuted, using a pulverizer, to a particle size range of 40 to 60 mesh (U.S. standard size). These particles comprised the delivery system.

A chemical assay of the powdered delivery system product showed that it contained 44% peppermint oil by weight based on the total product weight.

Over a period of ten months at room temperature in a clear, transparent jar the product showed no degradation. There was neither observable color change nor oxidation of flavor which was perceptible to the taste.

EXAMPLE II

Example I was repeated using 30 grams of synthetic spearmint oil instead of peppermnt oil. A chemical assay showed a 46% spearmint oil concentration (as carvone) based on the total product weight. The product had the same stability exhibited by the peppermint oil/aglinate delivery system of Example I.

EXAMPLE III

Example I was repeated using 50 grams of peppermint oil. The matric was filtered, frozen overnight, and then defrosted to remove excess water. After air drying the product assayed 59.6% by weight peppermint oil. The stability of the product was the same as that of the product of Example I.

EXAMPLE IV

Eighteen grams of sodium alginate solution (having a viscosity of 115 centipoise in 10% by weight aqueous solution at 75° C.) and 6 grams of xanthum gum were dissolved in 772 grams of distilled water and chilled to 5° C. Forty grams of peppermint oil (Madras) was then added while mixing in a high speed food blender until the oil droplets were in the 1 to 3 micron range. The emulsion was fed through a capillary positioned a few inches above a chilled (5° C.) calcium chloride solution (2% by weight) while drawing a vacuum on the calcium chloride solution. As the droplets of gel entered the calcium chloride solution they rapidly precipitated into substantially water insoluble particles or beads. A subsequent washing in distilled water and air drying for two days yielded free flowing off-white spherical particles containing entrapped peppermint oil. The particles assayed 58.5% flavor oil.

Upon hydration this product was softer than the product made using sodium alginate without xanthum gum.

EXAMPLE V

The process of Example 1 was repeated except that 125 grams of a sodium alginate solution which had a viscosity of 420 centipoise in a 10% by weight aqueous solution at 75° C. was used. To this solution was added 62.5 grams of peppermint oil (Rose Mitchum). The resultant calcium alginate/peppermint oil delivery system was freeze dried. The product retained its original fluffy characteristics and had a low bulk density. The product assayed 30.1% peppermint oil.

EXAMPLES VI & VII

In order to demonstrate the utility of the products of the present invention in a vehicle, chewing gum compositions were prepared using the delivery systems of Example I (44% peppermint flavor) and Example Y (30.1% peppermint flavor). The gums had the following composition.

| Ingredient | % By Weight VI | VII |
|---|---|---|
| Gum Base | 26.5 | 26.5 |
| Softener | 1.3 | 1.3 |
| Sugar 6X | 69.5 | 68.2 |
| Delivery System | | |
| (Example I) | 2.7* | — |
| (Example II) | — | 4.0* |

*1.2% flavor

The flavor composite was blended with the powdered sugar in a mixing kettle equipped with Sigma blades with mixing for three minutes at room temperature. The gum base was melted at about 90° C.–100° C. and mixed into the kettle along with the softener. Mixing was continued for about 5 minutes. The gum was discharged from the kettle and formed into sheets and cooled to room temperature.

A control gum was prepared in the same manner containing only unencapsulated, free peppermint oil (1.2% by weight) as the flavoring. Flavor chew-out studies were conducted using a group of five panelists who chewed the gum samples for ten minutes. The amount of flavor remaining in the bolus after chewing was determined by gas chromatography and the results recorded as percent of total flavor extracted. The results are shown in Table I.

TABLE I

Gum Chew-Out Studies

| Product | Flavor Extracted (As a % of total flavor) |
|---|---|
| Control Gum | 9% |
| Product using delivery of | |
| Example I | 40.5% |
| Example V | 72.7% |

At the end of the 10 minutes, the control gum no longer released flavor while the test gums continued to exhibit significant flavor release. A separate study with continued chewing showed that a gum using only the product of Example I as the flavor, continued to release flavor for nearly 20 minutes. All inventive test gums showed a delayed release of flavor of about 2 to 4 minutes. During the period of chew from 10 to 20 minutes, the rate of release of the control gum was relatively constant, showing absence of flavor release, as compared with chewing gums containing the inventive flavor delivery system.

FIG. I show the chewing gums containing a peppermint oil-calcium alginate flavor delivery system released 80% of the flavor; and about 20% of the flavor was released between the 10 to 20 minute chew period. The control gum showed a maximum flavor release of about 15%. Only a slight amount of that percentage was released after 10 minutes.

Flavor remaining in the gum bolus after chewing was determined by gas chromatograph.

It is apparent that the inventive delivery systems give superior active ingredient, e.g., flavor, release and prolongation over the prior art.

EXAMPLE VIII

The following examples further illustrate the preparation of calcium alginate entrapped flavor using various flavors and alginates. The results are tabluated in Table II.

TABLE II

FLAVOR ENTRAPMENT USING DIFFERENT FLAVORS AND MONOVALENT SALT SOLUTIONS

| Example | Sodium Alginate Weight grams | Flavor Oil Weight grams | % Entrapped[1] Flavor (w/w) | % Efficiency[2] of Entrapment | Method[3] Used: Example # |
|---|---|---|---|---|---|
| 6*  | 2.0  | 2.4+     | 47.2 | 86.5  | 1 |
| 7*  | 10.0 | 10.+++   | 46.3 | 92.6  | 1 |
| 8*  | 20.0 | 20.0++   | 39.9 | 79.8  | 1 |
| 9** | 30.0 | 30.0+    | 43.8 | 87.6  | 4 |
| 10**| 30   | 60.0+    | 67.1 | 100.6 | 4 |
| 11**| 30   | 76.0+    | 71.9 | 100.1 | 5 |
| 12**| 50   | 25+      | 28.1 | 84.4  | 1 |
| 13**| 50   | 25+      | 26.6 | 80.0  | 5 |
| 14**| 51   | 17+      | 18.4 | 73.6  | 1 |
| 15**| 51   | 17+      | 18.6 | 74.4  | 5 |
| 16**| 50   | 10+      | 9.7  | 58.2  | 1 |
| 17**| 50   | 10+      | 11.6 | 69.6  | 5 |

+Peppermint oil (Madras)
++Cinnamon oil (Cassia)
+++Menthol
[1]Based on actual assay amount of product
[2]Percent of flavor released
[3]Preparation carried out using method of Example indicated
*Sodium alginate having a viscosity of 115 Centipoise in a 1% solution at 75° C.
**Sodium alginate having a viscosity of 420 Centipoise in a 1% solution at 75° C.

EXAMPLE IX

Sodium alginate (40 grams) was placed in 760 grams of ice water to obtain a 5% hydrocolloid solution. The temperature of the water was maintained at about 0° to 5° C. to aid in obtaining a supersaturated solution which, in turn, yields a good dispersion. Thymol (40 grams, finely ground), saccharin acid powder (12 grams) and cinnamon oil (48 grams) were dispersed in the sodium alginate solution as active ingredients to be entrapped. The dispersion was homogenized using a high shear mixer while maintaining the low temperature of the aqueous medium. At this point 0.4N HCl (800 grams) was added as the precipitate initiating material and high shear mixing is continued. The precipitate readily formed, entrapping the thymol, saccharin acid and cinnamon oil therein. The precipitate was filtered off, washed and air dried. The resultant product was then ground to the desired particle size.

The product was assayed to determine the actual vs. theoretical amounts of the active ingredients, which indicates the degree of efficiency of entrapment. The results are shown below:

|  | Theoretical | Actual |
| --- | --- | --- |
| Thymol | 27.6% | 21.5% |
| Saccharin acid | 8.3% | 7.7% |
| Cinnamon oil | 33.1% | 32.5% |

It is apparent from the close correlation between theoretical and actual values that the entrapment process is very efficient.

EXAMPLE X

Seventeen (17) grams of sodium alginate was added to 574 grams of cold water (0° to 5° C.). To this hydrocolloid solution was added fine powdered thymol as the active material. Xanthan gum (6 grams) was added as a filler to enhance and soften the final texture of the precipitate. The dispersion was mixed at high shear, maintaining cold temperatures. About 600 grams of 0.2N HCl was added as the precipitate initiating material. The resultant precipitate rapidly formed entrapping the thymol within the matrix. The precipitate was filtered, washed and freeze dried. The resultant product was then assayed for actual vs. theoretical amounts of entrapped active ingredients. The results are shown below:

|  | Theoretical | Actual |
| --- | --- | --- |
| Thymol | 29.9% | 27.5% |

EXAMPLE XI

Sodium alginate (62.5 grams) was added to 1800 grams of ice water. To this hydrocolloid solution was added granulated thymol (40 grams), and peppermint oil (62.5 grams) to form a dispersion. The dispersion was homogenized using high shear mixing while maintaining the low water temperature. The dispersion was then fed through a nozzel and sprayed into 2000 grams of cold (0° to 5° C.) aqueous calcium chloride solution. The precipitate formed rapidly, entrapping the thymol and peppermint oil actives within. The precipitate was recovered, washed and dried. The assay results are as follows:

|  | Theoretical | Actual |
| --- | --- | --- |
| Thymol | 24.2% | 22.8% |
| Peppermint Oil | 37.9% | 35.7% |

EXAMPLE XII

Sodium alginate (62.5 grams) was added to 1800 grams of ice water. To this hydrocolloid solution was added granulated thymol (40 grams), and peppermint oil (62.5 grams) to form a dispersion. The dispersion was homogenized using high shear mixing while maintaining the low water temperature. The dispersion was then fed through a nozzle and sprayed into 2000 grams of cold (0° to 5° C.) aqueous calcium chloride solution. The precipitate formed rapidly, entrapping the thymol and peppermint oil actives within. The precipitate was recovered, washed and dried. The assay results are as follows:

|  | Theoretical | Actual |
| --- | --- | --- |
| Thymol | 24.2% | 22.8% |
| Peppermint Oil | 37.9% | 35.7% |

EXAMPLE XIII

A hydrocolloid solution containing 860 grams of water at 0° to 5° C. and 40 grams of sodium alginate was prepared. To this was added the following combination of active ingredients: 10 grams of N-acetyl-procianamide (NAPA) and 25 grams of spearmint oil. The resultant dispersion was mixed at low temperature until homogenous and followed by addition of calcium chloride (1000 grams of a 1% aqueous solution) as the precipitate initiating material. The precipitate formed rapidly, entrapping the actives within the matrix of the crosslinked bivalent alginate.

EXAMPLE XIV

A hydrocolloid solution containing 1160 grams of water at 0° to 5° C. and two grams of sodium alginate was prepared. About 5 grams of guaifenesin and 25 grams of peppermint oil were dispersed into the hydrocolloid solution as actives. The dispersion was mixed at high shear until homogenous, at which time 1000 grams of a 1% aqueous solution of calcium chloride was added as the precipitate initiating material. The precipitate was recovered, dried and washed to yield the resultant delivery system product.

EXAMPLE XV

A hydrocolloid solution containing 1500 grams of water (0° to 5° C.) and 62.5 grams of sodium alginate was prepared. Ten grams of psuedoephedrine HCl and 40 grams of peppermint oil were dispersed therein as active ingredients and the dispersion was mixed until uniform. To this dispersion was added 1500 grams of a 1% aqueous solution of calcium chloride. The precipitate formed readily and the resultant product successfully entrapped both active ingredients.

The invention being thus described, it will be obvious that the same may be varied in many ways. Such variations are not to be regarded as a departure from the spirit and scope of the invention and all such modifications are intended to be included within the scope of the claims.

We claim:

1. a process of preparing a particulate delivery system comprising:
   (i) forming an aqueous suspension of an insolubilized active ingredient and a monovalent cation salt of an algin or carageenen, wherein the insolubilized active ingredient is selected from the group consisting of drugs, favors, coloring agents, sweetening agents, perfumes, bulking agents and mixtures thereof;
   (ii) combining the aqueous suspension of the insolubilized active ingredient with a precipitate initiating material to form a polymeric matrix entrapping said active with the matrix interstices;
   (iii) rcovering the resultant product and drying to yield the delivery system.

2. The process of claim 1 wherein the precipitate initiating material contains a multivalent cation.

3. The process of claim 1 wherein the precipitate initiating material comprises an acid.

4. The process of claim 2 wherein the precipitate initiating material is selected from the group consisting of aluminum, calcium, copper, magnesium, zinc, manganese, iron and mixtures thereof.

5. The process of claim 4 wherein the precipitate initiating material is in solution prior to addition to the suspension of (i).

6. The process of claim 3 wherein the precipitate initiating material is selected from the group consisting of hydrochloric acid, nitric acid and sulfuric acid.

7. The process of claim 1 wherein the flavoring agent is selected from the group consisting of spearmint oil, cinnamon oil, oil of wintergreen (methy salicylate), peppermint oil, citrus oil, fruit essences, cinnamyl acetate, cinnamaldehyde, citral diethylacetal, dihyrocarvyl acetate, eugenyl formate, p-methyl-amisol and mixtures thereof.

8. The process of claim 1 wherein the drug is selected from the group consisting of mineral supplements, analgesics, antipyretics, antiarrhythmics, ion exchange resins, appetite supressants, vitamins, antiinflammatory substances, coronary dilators, cerebral dilators, peripheral vasodilators, anti-infectives, psychotropics, antimanics, stimulants, antihistamines, laxatives, decongestants, gastro-intestinal sedatives, antidiarrheal preparations, anti-anginal drugs, vasodilators, anti-hypertensive drugs, vasoconstrictors and migrane treatments, antibiotics, tranquilizers, antipsychotics, antitumor drugs, anticoagulants and antithrombotic drugs, hypnotics, sedatives, anti-emetics, anti-nauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, anti-uricemic drugs and mixtures thereof.

9. The process of claim 4 wherein the sweetening agents are selected from the group consisting of natural sweeteners and artificial sweeteners.

10. The process of claim 1 wherein the ratio of active ingredient to precipitate is about 5:1 to about 1:2.

11. The process of claim 10 wherein the ratio of active ingredient to precipitate is about 2:1 to about 1:1.

12. The process of claim 1 wherein the temperature of the aqueous suspension is such that the active ingredient neither crystallizes nor evaporates appreciably.

13. The process of claim 1 wherein the precipitated product is freeze dried and then thawed to form the delivery system.

14. The process of claim 1 wherein the precipitated product is freeze dried followed by air drying to form the delivery system.

15. A delivery system comprising:
   (a) an insolubolized active ingredient; and
   (b) a cross-linked multivalent cation alginate or multivalent cation carageenenate matrix; said delivery system prepared by the process of:
      (i) forming an aqueous suspension of the insolubolized active ingredient and a monovalent cation salt of an algin or carageenen;
      (ii) combining the aqueous suspension of the insolubolized active ingredient with a precipitate initiating material; and
      (iii) recovering a precipitated product and drying to form the delivery system.

16. The delivery system of claim 15 wherein the insolubolized active ingredient is selected from the group consisting of flavor agents, drugs, a coloring agent, perfumes, sweetening agents, bulking agents and mixtures thereof.

17. The delivery system of claim 15 wherein the precipitate initiating material is a multivalent cation or an acid.

18. The delivery system of claim 15 wherein the multivalent cation is selected from the group consisting of the salts of aluminum, calcium, copper, magnesium, zinc, iron, manganese, and mixtures thereof.

19. The delivery system of claim 17 wherein the multivalent cation salt is in aqueous solution.

20. A delivery system comprising:
   (a) an insolubolized active ingredient selected from the group consisting of flavoring agents, drugs, coloring agents, sweetening agents, perfumes, bulking agents and mixtures thereof; and
   (b) a cross-linked multivalent cation alginate or multivalent cation carageenenate matrix entrapping said insolubolized active ingredient.

21. The delivery system of claim 20 wherein the multivalent cation alginate or carageenenate is selected from the group consisting of the salts of aluminum, iron, calcium, copper, magnesium, zinc, manganese and mixtures thereof.

22. The delivery system of claim 20 wherein the particle size of the active ingredient is about 1 to about 10 microns.

23. The delivery system of claim 20 wherein the ratio of active ingredient to matrix material is about 5:1 to about 1:2.

24. A chewing gum composition containing the delivery system of claim 20.

25. A pharmaceutical preparation containing the delivery system of claim 20.

26. A denture adhesive containing the delivery system of claim 20.

* * * * *

UNITED STATES PATENT AND TRADEMARK OFFICE
CERTIFICATE OF CORRECTION

PATENT NO. : 4,695,463

DATED : September 22, 1987

INVENTOR(S) : Robert K. Yang

It is certified that error appears in the above-identified patent and that said Letters Patent is hereby corrected as shown below:

In Claim 1, line 15, the phrase "with the matrix" should read --within the matrix--.

Signed and Sealed this

Nineteenth Day of April, 1988

Attest:

DONALD J. QUIGG

*Attesting Officer*     *Commissioner of Patents and Trademarks*